United States Patent
Cho et al.

(10) Patent No.: US 9,121,004 B2
(45) Date of Patent: Sep. 1, 2015

(54) CELL CULTURE UNIT AND CELL CULTURE DEVICE INCLUDING THE SAME

(75) Inventors: Young-Ho Cho, Daejeon (KR); Tae-Yoon Kim, Seoul (KR); Dong-Woo Lee, Daejeon (KR); Sang-Jin Kim, Gyeonggi-do (KR); Yong-Soo Oh, Gyeonggi-do (KR); Bo-Sung Ku, Gyeonggi-do (KR)

(73) Assignee: Korea Advanced Institute of Science and Technology, Daejeon (KR)

(*) Notice: Subject to any disclaimer, the term of this patent is extended or adjusted under 35 U.S.C. 154(b) by 0 days.

(21) Appl. No.: 13/581,028

(22) PCT Filed: Feb. 24, 2011

(86) PCT No.: PCT/KR2011/001277
§ 371 (c)(1),
(2), (4) Date: Aug. 24, 2012

(87) PCT Pub. No.: WO2011/105818
PCT Pub. Date: Sep. 1, 2011

(65) Prior Publication Data
US 2012/0315694 A1  Dec. 13, 2012

(30) Foreign Application Priority Data
Feb. 26, 2010 (KR) .................. 10-2010-0018161

(51) Int. Cl.
*C12M 1/14* (2006.01)
*C12M 3/06* (2006.01)
*C12M 1/00* (2006.01)

(52) U.S. Cl.
CPC .............. *C12M 23/16* (2013.01); *C12M 29/04* (2013.01)

(58) Field of Classification Search
CPC ....... C12M 25/02; C12M 23/16; C12M 29/04
USPC .......... 435/297.1, 297.5; 210/248, 246, 416.1
See application file for complete search history.

(56) References Cited

U.S. PATENT DOCUMENTS

| | | | | |
|---|---|---|---|---|
| 4,215,198 A | * | 7/1980 | Gordon ...................... | 435/287.4 |
| 5,512,480 A | * | 4/1996 | Sandstrom et al. ......... | 435/299.1 |
| 6,576,458 B1 | * | 6/2003 | Sarem et al. ............... | 435/286.5 |
| 2002/0127630 A1 | * | 9/2002 | DiGuiseppi et al. ....... | 435/287.1 |
| 2006/0216819 A1 | | 9/2006 | Yasuda et al. | |
| 2010/0009460 A1 | * | 1/2010 | Clark et al. .................. | 436/180 |

FOREIGN PATENT DOCUMENTS

| | | |
|---|---|---|
| JP | 2004089137 A | 3/2004 |
| JP | 2004089138 A | 3/2004 |

(Continued)

*Primary Examiner* — Nathan Bowers
*Assistant Examiner* — Timothy Barlow
(74) *Attorney, Agent, or Firm* — Locke Lord LLP; Christopher J. Capelli; Judy Naamat

(57) ABSTRACT

There is provided a cell culture device, which includes a plurality of cell culture units, in which the cell culture unit includes: a cell culture tub that defines a culture space for cultivating cells, contains culture medium in the culture unit, and has an air layer above the culture medium; a drainage channel that is connected to the cell culture tub to discharge used culture medium to the integral drainage channel; an open culture medium reservoir that supplies new culture medium into the cell culture tub; and a droplet generator that is disposed between the cell culture tub and the open culture medium reservoir and supplies the culture medium from the open culture medium reservoir to the cell culture tub, using negative pressure of the air layer generated when the used culture medium is discharged.

8 Claims, 2 Drawing Sheets

(56) References Cited

FOREIGN PATENT DOCUMENTS

| | | |
|---|---|---|
| JP | 2006345714 A | 12/2006 |
| JP | 2007312668 A | 12/2007 |
| JP | 2009291097 A | 12/2009 |
| KR | 10-2006-0117945 | 11/2006 |
| KR | 10-0737295 | 7/2007 |
| KR | 10-0766619 | 10/2007 |
| WO | 2005047464 A2 | 5/2005 |

* cited by examiner

CELL CULTURE UNIT AND CELL CULTURE DEVICE INCLUDING THE SAME

CROSS-REFERENCES TO RELATED APPLICATIONS

This application is a 35 U.S.C. §371 U.S. national entry of International Application PCT/KR2011/001277 (WO 2011/105818) having an International filing date of Feb. 24, 2011, which claims under 35 U.S.C. §119(a) the benefit of Korean Application No. 10-2010-0018161, filed Feb. 26, 2010, the entire contents of which are incorporated herein by reference.

TECHNICAL FIELD

The present invention relates to a cell culture unit and a cell culture device including the same, and more particularly, a cell culture unit that can constantly maintain a cell proliferation rate and a cell activity, and a cell culture device including the cell culture unit.

BACKGROUND ART

In general, cell culture means that cell tissue is extracted from multi-cellular organism under an aseptic condition, and then cultured and proliferated in a culture medium.

A culture of group of cells, a culture of a small organ, and a culture of a phyton from one cell are all possible through the use of various cell culture methods.

A cell culture may be performed for various purposes, such as the collection of additional by-products of a cell s metabolism, the production of virus vaccine, a pre-meditated cell culture for producing artificial organs, the production of medicine and medical supplies by the genetic manipulation of animal cells, or breeding by the blending of plant cells.

Plant cells can be easily cultured due to a high viability generated by their photosynthesis. However, a culture of animal cells generally needs a culture ground containing nutrients, such as amino acid, sugars, mineral salts, vitamins, etc. In order to effectively culture animal cells, various culture methods according to each cell s properties have been developed according to the properties of each cell, such as hybrodomas or embryonic stem cells.

However, there are methods which have been used until now for the mass culture of adhesive cells, such as fibroblastoid or epithelial-like cells. The yield of a culture according to the existing methods is low and a long period culture is difficult.

A certain space for culturing cells and a cell culture medium for supplying nutrients to cells are needed to culture cells. In particular, the cell culture medium and various gases should be injected into the culture space to be used in culturing cells, and then changed regularly in order to maintain cellular tissues in a fresh condition. Therefore, the cell culture device should be configured to easily perform the continuous supplying and wasting processes of the culture medium and various gases.

To change the culture medium, the culture medium is sucked into a pipette, injected into the culture space, and then is wasted by using the pipette. However, a method of using a pipette has a high risk of losing cells, and cannot easily change the culture medium, so the method of using a pipette is inefficient.

DISCLOSURE OF INVENTION

Technical Problem

An aspect of the present invention provides a cell culture unit that can maintain a constant cell proliferation rate and a cell activity, and a cell culture device including the same.

Solution to Problem

According to an aspect of the present invention, there is provided a cell culture unit, which includes: a cell culture tub that defines a culture space for cultivating cells, contains culture medium in the culture space, and has an air layer above the culture medium; a drainage channel that is connected to the cell culture tub to discharge used culture medium; an open culture medium reservoir that supplies new culture medium into the cell culture tub; and a droplet generator that is disposed between the cell culture tub and the open culture medium reservoir and supplies the culture medium from the open culture medium reservoir to the cell culture tub, using negative pressure of the air layer generated when the used culture medium is discharged.

The cell culture tub may have grooves where the cells proliferate in three-dimensional lump shapes.

The drainage channel may have a side channel formed along the edge of the cell culture tub and a straight channel connected with the side channel.

One or more drainage channels may be formed.

A valve for selectively opening/closing the drainage channel may be provided in the drainage channel.

The open culture medium reservoir may have an inclined side.

The droplet generator may have one or more droplet outlets through which the culture medium is supplied in droplet shapes from the open culture medium reservoir to the cell culture tub.

The droplet generator may be formed of a porous thin layer.

According to another aspect of the present invention, there is provided a cell culture device, which includes: a plurality of cell culture units; and integral drainage channel connecting each of the cell culture units, in which the cell culture unit includes: a cell culture tub that defines a culture space for cultivating cells, contains culture medium in the culture space, and has an air layer above the culture medium; a drainage channel that is connected to the cell culture tub to discharge used culture medium to the integral drainage channel; an open culture medium reservoir that supplies new culture medium into the cell culture tub; and a droplet generator that is disposed between the cell culture tub and the open culture medium reservoir and supplies the culture medium from the open culture medium reservoir to the cell culture tub, using negative pressure of the air layer generated when the used culture medium is discharged.

The integral drainage channel may be provided with a resistor to adjust the flow rate of each drainage channel.

Advantageous Effects of Invention

As set forth above, according to exemplary embodiments of the invention, the culture medium is contained in the open reservoir and supplied to the cell culture tub through the droplet generator. Therefore, it is possible to easily supply a variety of samples and prevent the culture medium or sample from being contaminated by dispersion.

Further, since it is possible to remove wastes created from the cells themselves by flowing the used culture medium through the drainage channel, it is possible to constantly keep the concentration of by-products created by the cells in the culture medium. Accordingly, it is possible for cells to proliferate under conditions similar to the inside of a human body. This improves reliability in vitro diagnosis, or a toxicity test of drugs or raw materials of cosmetics.

BRIEF DESCRIPTION OF DRAWINGS

The above and other aspects, features and other advantages of the present invention will be more clearly understood from the following detailed description taken in conjunction with the accompanying drawings, in which.

BEST MODE FOR CARRYING OUT THE INVENTION

Figure 1:
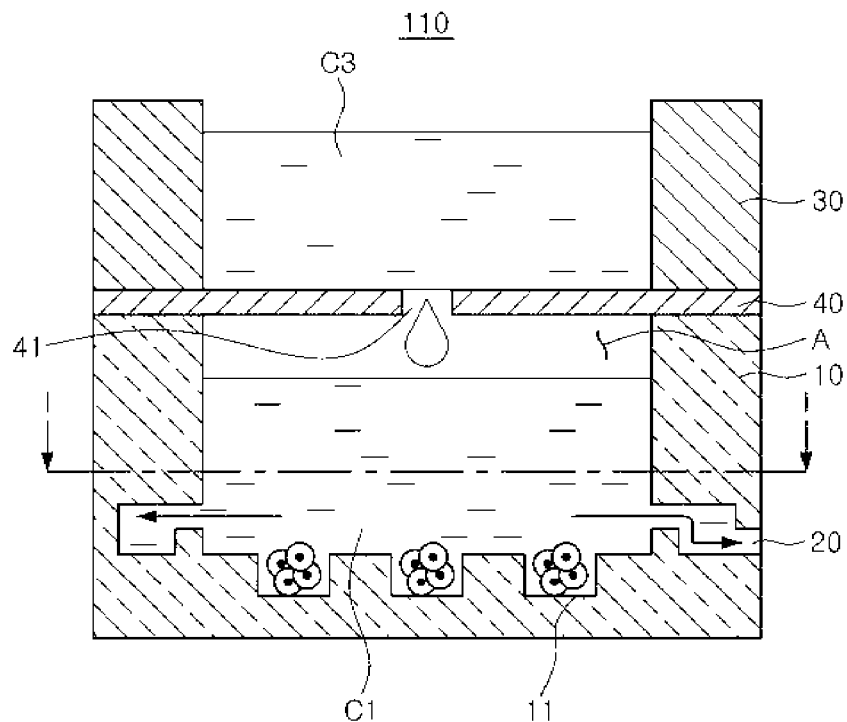
FIG. 1 is schematic side cross-sectional view showing a cell culture unit according to an embodiment of the present invention.

Exemplary embodiments of the present invention will now be described in detail with reference to the accompanying drawings. However, the embodiments of the present invention may be modified in various ways and the scope of the present invention is not limited to the following embodiments. Exemplary embodiments of the present invention are provided so that those skilled in the art may more completely understand the present invention. Therefore, the shape and size of the components may be exaggerated in the drawings for more clear explanation and the components indicated by the same reference numerals in the drawings are the same component.

Figure 2:
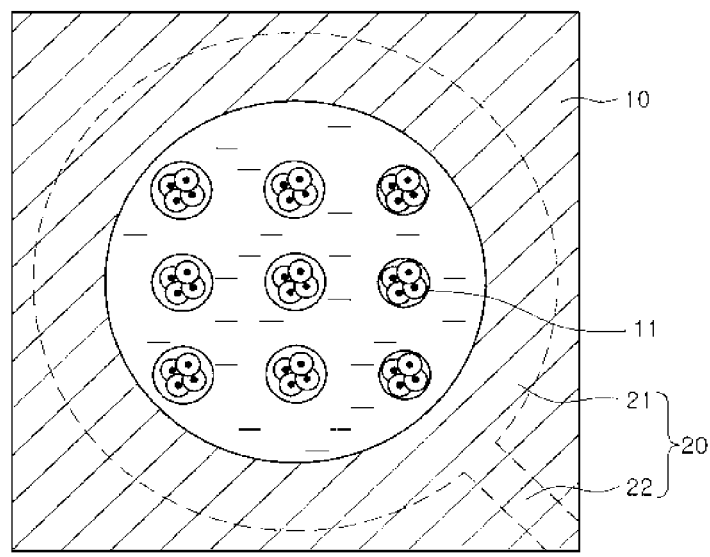
FIG. 2 is a schematic vertical cross-sectional view showing the cell culture unit, taken along line A-A' of FIG. 1.

FIG. 1 is schematic side cross-sectional view showing a cell culture unit according to an embodiment of the present invention and FIG. 2 is a schematic vertical cross-sectional view showing the cell culture unit, taken along line A-A' of FIG. 1.

Referring to FIGS. 1 and 2, a cell culture unit according to an embodiment of the present invention includes a cell culture tub 10, a drainage channel 20, an open culture reservoir 30, and a droplet generator 40.

The cell culture tub 10 defines a culture space for cultivate cells and the culture space is filled with culture medium C1.

The culture medium C1 is filled in the culture space of the culture tub 10, but is not filled in the entire culture space. Accordingly, an air layer A is formed above the culture medium.

The cell tub 10 is not limited to a specific structure, as long as it can define a culture space, and may have various shapes, such as cylindrical and prism shapes.

The cell culture tub may have grooves 11 on the bottom. In the grooves 11, cells can proliferate in a three-dimensional lump shape.

The drainage channel 20 through which the culture medium is discharge is connected to the cell culture tub 10. Used culture medium used to proliferate and activate the cells is discharged through the drainage channel. One or more drainage channels may be formed. Further, it is possible to control the flow rate of the discharged culture medium by adjusting the length and cross-sectional area of the drainage channel.

The drainage channel 20 may have a side channel 21 formed along the edge of the cell culture tub and a straight channel 22 connected with the side channel. The used culture medium in the cell culture tub can be discharged at a uniform flow rate through the side channel. Since the flow of the culture medium influences the proliferation and activation of the cells, it is important that the flow rate is uniform.

Further, a valve (not shown) for selectively opening/closing the drainage channel may be provided in the drainage channel 20.

The open culture reservoir 30 supplies the cell culture tub 10 with new culture medium C. The open culture medium reservoir is partially open to the outside.

The droplet generator 40 is disposed between the cell culture tub 10 and the open culture reservoir 30 to supply new culture medium from the open culture reservoir to the cell culture tub, as the used culture medium is discharged.

In detail, as the used culture medium is discharged through the drainage channel 20, negative pressure is generated while the air layer A increases in the cell culture tub, such that the new culture medium in the open culture medium reservoir 30 is supplied to the cell culture tub 10 in a droplet shape through a droplet outlet 41 of the droplet generator 40. The droplet generator 40 may be formed of a porous thin layer.

In this embodiment, new culture medium is supplied in quantities equal to those of the culture medium discharged out of the cell culture tub by the open reservoir. Therefore, the cell culture environment is maintained with a log of nutrition and little waste.

The existing cell culture methods cultivate cells in stationary culture medium and supply the culture medium to a cell culture region through a pipe or a channel connected with a closed reservoir.

According to those methods, since the pipe or the channel is directly connected with the cell culture region, the culture medium or samples can be contaminated by dispersion.

According to this embodiment, however, the culture medium is contained in an open reservoir and supplied to the cell culture tub through the droplet generator. Therefore, it is possible to easily supply a variety of samples and prevent the culture medium or sample from being contaminated by dispersion.

Further, since it is possible to remove wastes created from the cells themselves by flowing the used culture medium through the drainage channel, it is possible to constantly keep the concentration of by-products created by the cells in the culture medium. Accordingly, it is possible to for cells to proliferate under conditions similar to the inside of a human body. This improves reliability in vitro diagnosis, or a toxicity test of drugs or raw materials of cosmetics.

Figure 3:
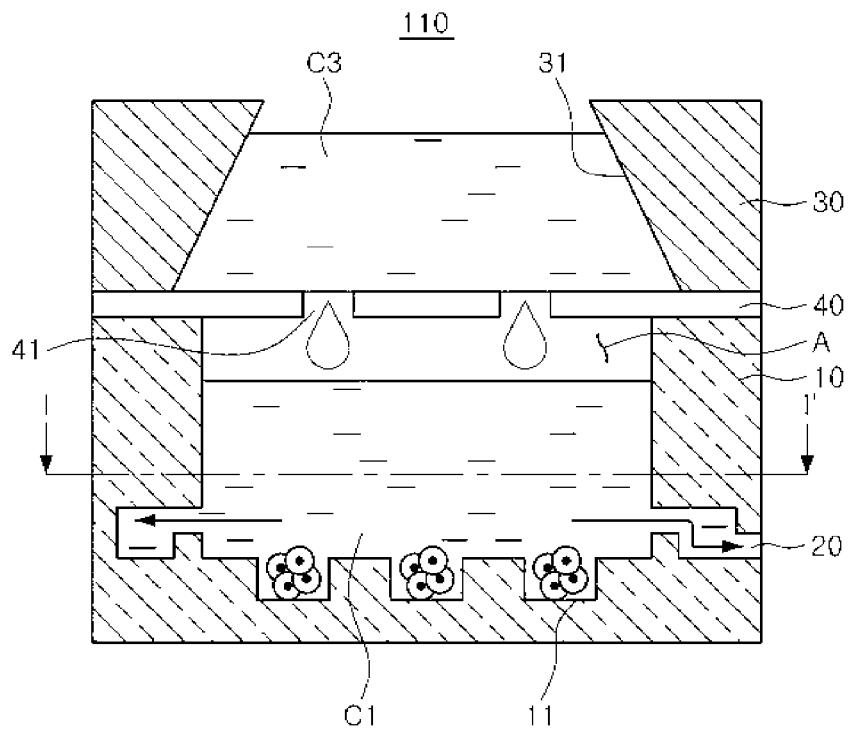
FIG. 3 is a schematic cross-sectional view showing a cell culture unit according to another embodiment of the present invention.

FIG. 3 is a schematic cross-sectional view showing a cell culture unit according to another embodiment of the present invention.

The same reference numerals as in the above embodiment indicate the same component and the other components are mainly described.

A cell culture unit according to this embodiment includes a cell culture tub 10, a drainage channel 20, an open culture medium reservoir 30, and a droplet generator 40.

The open culture medium reservoir 30 may have an inclined side 31. The side 31 may be formed to become narrow from the cell culture tub toward the outside. Therefore, it is possible to prevent the culture medium from spattering or vaporizing in the process of injecting new culture medium into the open culture medium reservoir.

Further, the droplet generator 40 disposed between the cell culture unit 10 and the open cell culture medium reservoir 30 may have one or more droplet outlets 41.

Figure 4:
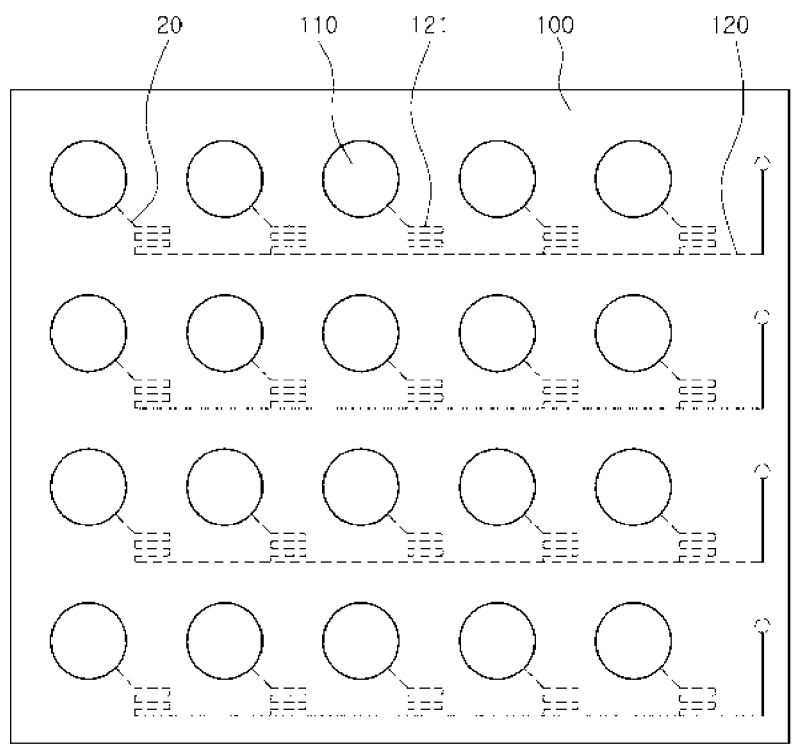
FIG. 4 is a schematic upper plan view showing a cell culture device according to an embodiment of the present invention.

FIG. 4 is a schematic upper plan view showing a cell culture device according to an embodiment of the present invention.

Referring to FIG. 4, a cell culture device according to this embodiment includes a plurality of cell culture units 110 and integral drainage channels 120 connecting each of the cell culture units.

The plurality of cell culture units may be formed on a substrate 100.

The cell culture unit, as described above, includes a cell culture tub 10, a drainage channel 20, an open culture medium reservoir 30, and a droplet generator 40.

The drainage channels are integrated by the integral drainage channel 120.

The integral drainage channel 120 may be provided with a resistor to adjust the flow rate of each drainage channel. It is possible to maintain uniform flow rate of the culture medium discharged from the cell culture units by adjusting the resistance value of the resistor.

Therefore, it is possible to keep the culture environments of each cell culture unit the same, or produce cell culture environments in accordance with designed conditions for each cell culture unit.

While the present invention has been shown and described in connection with the exemplary embodiments, it will be apparent to those skilled in the art that modifications and variations can be made without departing from the spirit and scope of the invention as defined by the appended claims.

The invention claimed is:

1. A cell culture unit, comprising:
a cell culture tub that defines a culture space for cultivating cells and has an air layer above the culture medium;
a drainage channel that is connected to the cell culture tub to discharge used culture medium;
an open culture medium reservoir that supplies new culture medium into the cell culture tub; and
a droplet generator formed of a porous thin layer that is disposed between the cell culture tub and the open culture medium reservoir and supplies the culture medium from the open culture medium reservoir to the cell culture tub, using negative pressure of the air layer generated when the used culture medium is discharged from the cell culture tub so that an amount of the culture medium supplied from the open culture medium reservoir into the cell culture tub is substantially equal to an amount of the culture medium discharged from the cell culture tub,
wherein the cell culture tub contains culture medium in the culture space and has wells separated from each other in which the cells proliferate in three-dimensional agglomerations, and the wells and the droplet generator are disposed separately.

2. The cell culture unit of claim 1, wherein the drainage channel has a side channel formed along the edge of the cell culture tub and a straight channel connected with the side channel.

3. The cell culture unit of claim 1, wherein one or more drainage channels are formed.

4. The cell culture unit of claim 1, wherein a valve for selectively opening/closing the drainage channel is provided in the drainage channel.

5. The cell culture unit of claim 1, wherein the open culture medium reservoir has an inclined side.

6. The cell culture unit of claim 1, wherein the droplet generator has one or more droplet outlets through which the culture medium is supplied in droplet shapes from the open culture medium reservoir to the cell culture tub.

7. A cell culture device, comprising:
a plurality of cell culture units; and
integral drainage channels connecting each of the cell culture units, wherein the cell culture unit includes:
a cell culture tub that defines a culture space for cultivating cells and has an air layer above the culture medium; a drainage channel that is connected to the cell culture tub to discharge used culture medium to the integral drainage channel; an open culture medium reservoir that supplies new culture medium into the cell culture tub; and a droplet generator that is disposed between the cell culture tub and the open culture medium reservoir and supplies the culture medium from the open culture medium reservoir to the cell culture tub, using negative pressure of the air layer generated when the used culture medium is discharged from the cell culture tub so that an amount of the culture medium supplied from the open culture medium reservoir into the cell culture tub is substantially equal to an amount of the culture medium discharged from the cell culture tub, wherein the cell culture tub contains culture medium in the culture space and has wells separated from each other where the cells proliferate in three-dimensional agglomerations, and the wells and the droplet generator are disposed separately.

8. The cell culture device of claim 7, wherein the integral drainage channel is provided with a resistor to adjust the flow rate of each drainage channel.

* * * * *